US008292901B2

(12) United States Patent
Auerbach et al.

(10) Patent No.: US 8,292,901 B2
(45) Date of Patent: Oct. 23, 2012

(54) UTERINE MANIPULATORS AND RELATED COMPONENTS AND METHODS

(75) Inventors: Robert D. Auerbach, Madison, CT (US); Peter K. Arneson, Cheshire, CT (US); Charles Sherts, Westport, CT (US)

(73) Assignee: CooperSurgical, Inc., Trumbull, CT (US)

( * ) Notice: Subject to any disclaimer, the term of this patent is extended or adjusted under 35 U.S.C. 154(b) by 214 days.

(21) Appl. No.: 12/767,967

(22) Filed: Apr. 27, 2010

(65) Prior Publication Data

US 2010/0305578 A1    Dec. 2, 2010

Related U.S. Application Data

(60) Provisional application No. 61/181,522, filed on May 27, 2009.

(51) Int. Cl.
*A61B 17/42* (2006.01)

(52) U.S. Cl. ......................................... 606/119; 600/185

(58) Field of Classification Search .................. 606/119, 606/135, 137, 191, 193, 198; 128/832, 842; 600/185, 201, 211
See application file for complete search history.

(56) References Cited

U.S. PATENT DOCUMENTS

| 1,856,295 A | 5/1932 | Sovatkin |
|---|---|---|
| 2,186,143 A | 1/1940 | Neugass |
| 2,456,806 A | 12/1948 | Wolffe |
| 2,744,708 A | 5/1956 | Bedford, Jr. |
| 3,131,690 A | 5/1964 | Innis et al. |
| 3,153,267 A | 10/1964 | Rowland, Jr. |
| 3,196,865 A | 7/1965 | Rose |
| 3,749,088 A | 7/1973 | Kohlmann |
| 3,766,909 A | 10/1973 | Ozbey |
| 3,769,983 A | 11/1973 | Merav |
| 3,877,433 A | 4/1975 | Librach |
| 3,948,270 A | 4/1976 | Hasson |
| 4,022,208 A | 5/1977 | Valtchev |
| 4,066,071 A | 1/1978 | Nagel |
| 4,323,057 A | 4/1982 | Jamieson |
| 4,430,076 A | 2/1984 | Harris |
| 4,533,349 A | 8/1985 | Bark |
| 4,562,832 A | 1/1986 | Wilder et al. |
| 4,597,030 A | 6/1986 | Brody et al. |
| 4,627,421 A | 12/1986 | Symbas et al. |
| 4,775,362 A | 10/1988 | Kronner |
| 4,823,167 A | 4/1989 | Manska et al. |
| 4,981,355 A | 1/1991 | Higgins |

(Continued)

FOREIGN PATENT DOCUMENTS

WO    WO 2009/078953    6/2009

OTHER PUBLICATIONS

Culligan et al., "Long-Term Success of Abdominal Sacral Colpopexy Using Synthetic Mesh," Am. J. Obstet. Gynecol., Dec. 2002.

*Primary Examiner* — Victor Nguyen
(74) *Attorney, Agent, or Firm* — Fish & Richardson P.C.

(57) ABSTRACT

A uterine manipulator tip includes a finger and an expandable member. The finger is configured to be confined within a cervix. The expandable member is carried by the finger and is configured to engage a cervical canal between an internal cervical os and an external cervical os of the cervix.

25 Claims, 10 Drawing Sheets

U.S. PATENT DOCUMENTS

| | | | |
|---|---|---|---|
| 4,996,974 A | 3/1991 | Ciarlei | |
| 4,997,419 A | 3/1991 | Lakatos et al. | |
| 5,104,377 A | 4/1992 | Levine | |
| 5,181,842 A | 1/1993 | Sunderland et al. | |
| 5,209,754 A | 5/1993 | Ahluwalia | |
| 5,232,443 A | 8/1993 | Leach | |
| 5,237,985 A | 8/1993 | Hodgson et al. | |
| 5,242,240 A | 9/1993 | Gorham | |
| 5,273,026 A | 12/1993 | Wilk | |
| 5,409,496 A | 4/1995 | Rowden et al. | |
| 5,431,662 A | 7/1995 | Nicholas | |
| 5,520,698 A | 5/1996 | Koh | |
| 5,540,700 A | 7/1996 | Rowden et al. | |
| 5,624,399 A | 4/1997 | Ackerman | |
| 5,690,617 A | 11/1997 | Wright | |
| 5,810,806 A | 9/1998 | Ritchart et al. | |
| 5,827,289 A * | 10/1998 | Reiley et al. | 606/86 R |
| 5,835,657 A | 11/1998 | Suarez et al. | |
| 5,840,077 A * | 11/1998 | Rowden et al. | 606/119 |
| 6,068,121 A | 5/2000 | McGlinch | |
| 6,080,118 A | 6/2000 | Blythe | |
| 6,328,729 B1 | 12/2001 | Jervis | |
| 6,348,036 B1 | 2/2002 | Looney et al. | |
| 6,682,100 B2 | 1/2004 | Wood et al. | |
| 6,741,895 B1 | 5/2004 | Gafni et al. | |
| 6,752,819 B1 | 6/2004 | Brady et al. | |
| 6,932,759 B2 | 8/2005 | Kammerer et al. | |
| 7,052,453 B2 | 5/2006 | Presthus et al. | |
| 2003/0195386 A1 | 10/2003 | Thierfelder et al. | |
| 2003/0220538 A1 | 11/2003 | Jacquetin | |
| 2004/0230092 A1 | 11/2004 | Thierfeld et al. | |
| 2005/0065395 A1 | 3/2005 | Mellier | |
| 2006/0015001 A1 | 1/2006 | Staskin et al. | |
| 2006/0199994 A1 | 9/2006 | Inman et al. | |
| 2007/0129615 A1 | 6/2007 | Backman et al. | |
| 2008/0221590 A1 | 9/2008 | Ikeda et al. | |
| 2010/0106163 A1 | 4/2010 | Blair et al. | |
| 2010/0152749 A1 | 6/2010 | Von Pechmann et al. | |
| 2010/0168784 A1 | 7/2010 | Pustilnik | |
| 2010/0179575 A1 | 7/2010 | Von Pechmann et al. | |
| 2010/0280309 A1 | 11/2010 | Von Pechmann | |

* cited by examiner

UTERINE MANIPULATORS AND RELATED COMPONENTS AND METHODS

CROSS-REFERENCE TO RELATED APPLICATIONS

This application claims the benefit of U.S. application Ser. No. 61/181,522, filed on May 27, 2009.

TECHNICAL FIELD

This disclosure relates to uterine manipulators and related components and methods.

BACKGROUND

Uterine manipulators are medical instruments that are used for manipulating (e.g., moving or repositioning) a patient's uterus during medical procedures. Such procedures include surgical procedures such as laparoscopic gynecologic surgery, e.g., total laparoscopic hysterectomy (TLH) surgery.

Instruments of this kind often include a proximal portion that remains external to the patient's body during use and a distal portion that is inserted into the patient's body. The proximal portion typically provides for manipulation of the instrument during use. The distal portion often includes a tip that is sized to be inserted into and/or engage a uterus. Generally, the distal portion of the instrument is advanced through the vaginal cavity and into the uterus. With the distal portion inserted within a uterus, the uterus can be manipulated through surgeon or physician controlled movements of the proximal portion. Following completion of a procedure, the instrument is removed from the patient's body via the vaginal cavity.

SUMMARY

In general, this disclosure relates to uterine manipulators and related components and methods. The uterine manipulators can be used, for example, for manipulating a patient's uterus during gynecological surgery and/or gynecological diagnostic procedures.

In one aspect, a uterine manipulator tip includes a finger and an expandable member. The finger is configured to extend within a cervix. The expandable member is carried by the finger and is configured to engage a cervical canal between an internal cervical os and an external cervical os of the cervix.

In another aspect, a uterine manipulator includes a uterine manipulator handle and a manipulator tip. The manipulator tip is configured to be coupled to the handle. The manipulator tip includes a finger and an expandable member. The finger is configured to extend within a cervix. The expandable member is carried by the finger and is configured to engage a cervical canal between an internal cervical os and an external cervical os of the cervix.

In a further aspect, a method includes inserting a uterine manipulator including a manipulator handle and a manipulator tip into a vaginal cavity such that a finger of the manipulator tip extends into a cervix, and then expanding an expandable member carried by the finger, thereby causing the expandable member to engage a cervical canal between an internal cervical os and an external cervical os of the cervix.

In yet another aspect, a uterine manipulator tip includes a finger and an anchor member. The finger is configured to extend within a cervix. The anchor member is carried by the finger and is configured to anchor to a cervical canal between an internal cervical os and an external cervical os of the cervix. The finger and the anchor member are sized to fit within a cervix without extending into a uterine cavity.

Embodiments of the disclosed methods, systems, and devices may include one or more of the following features.

In some embodiments, the uterine manipulator tip can also include a base that is configured to be releasably attached to a uterine manipulator handle. In some such embodiments, the finger extends outwardly from a first surface of the base.

The finger can have a length of about 10 mm to about 50 mm along a longitudinal axis of the finger.

The finger can have a diameter of about 1 mm to about 6 mm.

The expandable member can have an expanded diameter of about 3 mm to about 26 mm.

The expandable member can have an expanded diameter of about 2 mm to about 20 mm greater than the diameter of the finger.

The expandable member can have a contracted diameter of about 1.5 mm to about 9 mm.

The expandable member can have a contracted diameter of about 0.5 mm to about 3 mm greater than the diameter of the finger.

The expandable member can have a length of about 1 cm to about 4 cm along a longitudinal axis of the expandable member.

In some embodiments, the expandable member is a balloon.

In some cases, the expandable member has an elliptospheric shape when expanded.

In some embodiments, the expandable member can include a textured surface for enhanced grip. Alternatively or additionally, the expandable member can include a surface treatment (e.g., a tacky coating) for enhanced grip.

In some embodiments, the uterine manipulator tip also includes a rod having a distal end extending within the finger providing the finger with increased resistance to bending.

The manipulator handle can include a tip hub that is configured to releasably receive and support the manipulator tip. In some cases, for example, the manipulator handle includes an elongate frame and a tip hub. The elongate frame has a proximal end portion and a distal end portion. The distal end portion is configured to be inserted into a vagina. The tip hub is configured to releasably receive and support the manipulator tip. The tip hub is pivotally connected to the distal end portion of the frame.

The manipulator handle can also include a grip that is pivotally connected to the proximal end portion of the frame. The grip is movable relative to the frame to control relative movements of the tip hub.

In some embodiments, the uterine manipulator includes a cup that is configured to be coupled to the manipulator handle. The cup includes a first open end that is configured to receive a cervix. In some cases, the cup is configured to be coupled to the manipulator handle via the manipulator tip.

In some embodiments, the uterine manipulator also includes a vaginal occluder. The vaginal occluder is configured to be coupled to the manipulator handle. The vaginal occluder is operable to inhibit the passage of fluid (i.e., liquid or gas) through a vaginal cavity. The vaginal occluder can be configured to be coupled to the manipulator handle via the manipulator tip.

Methods can also include repositioning (e.g., anteverting or retroverting) a uterus with the uterine manipulator assembly while the expandable member is engaged with the cervical canal.

Expanding the expandable member can include inflating the expandable member with a fluid (i.e., a liquid or a gas).

Embodiments can include one or more of the following advantages.

Providing a uterine manipulator that is capable of repositioning a uterus without any portion of the uterine manipulator entering the uterine cavity can help to reduce or prevent contact with and dissemination of cancerous cells within the uterine cavity. This can be beneficial in situations where cancerous cells are present in tissue within or surrounding the uterine cavity (e.g., in a portion of the fundus forming the uterine cavity) since this can help to avoid or reduce the risk of contact with and, as a result, displacement and spreading of the cancerous tissue during uterine manipulation.

Similarly, providing a uterine manipulator with a manipulator tip that is capable of engaging a cervical canal in such a manner as to allow for repositioning of a uterus without entering or engaging the uterine cavity can help to reduce or avoid the disturbance of tissues within the uterine cavity. Because the uterine manipulator does not enter or engage the uterine cavity, likelihood of displacing cancerous cells present in the tissue within or surrounding the uterine cavity (e.g., in the fundus) is reduced.

Other aspects, features, and advantages are in the description, drawings, and claims.

DETAILED DESCRIPTION

Figure 1:
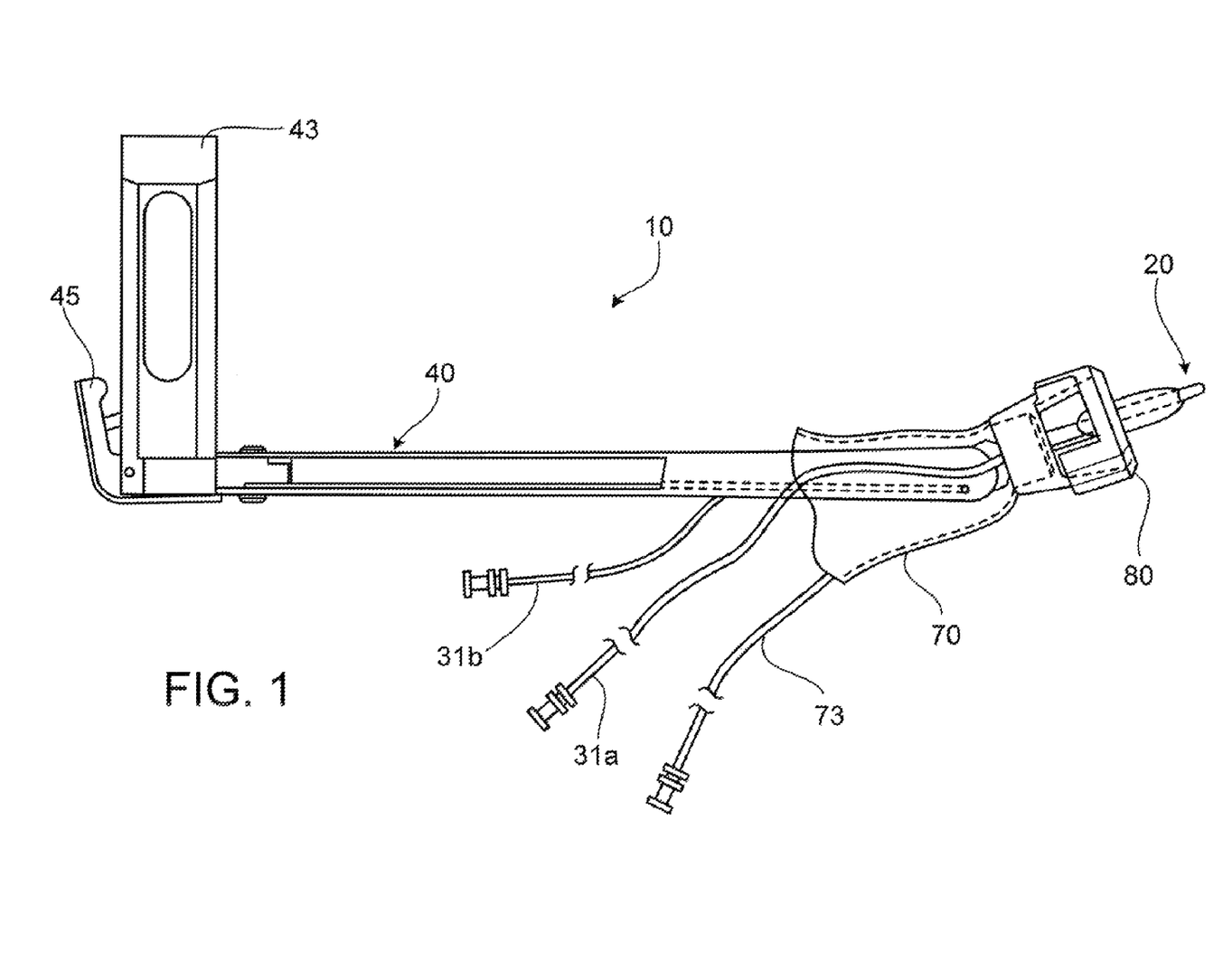
FIG. 1 is a side view of a uterine manipulator.

FIG. 1 illustrates a uterine manipulator 10 adapted for insertion into a vaginal cavity for use in female pelvic surgical procedures. The uterine manipulator 10 includes a manipulator tip 20 releasably coupled to a manipulator handle 40, a vaginal occluder 70 releasably coupled to the manipulator tip 20, and a cervical cup 80. The manipulator tip 20 is configured to extend within a cervix, and to engage a cervical canal to aid in repositioning a uterus without any part of the manipulator tip 20 ever entering the uterine cavity, which may help to avoid the disturbance of tissues within or surrounding the uterine cavity. This can be beneficial in situations where cancerous cells are present in tissue surrounding the uterine cavity (e.g., in a portion of the fundus forming the uterine cavity) since this can help to avoid or reduce the risk of contact with and, as a result, displacement and spreading of the cancerous tissue during uterine manipulation.

Figure 2A:
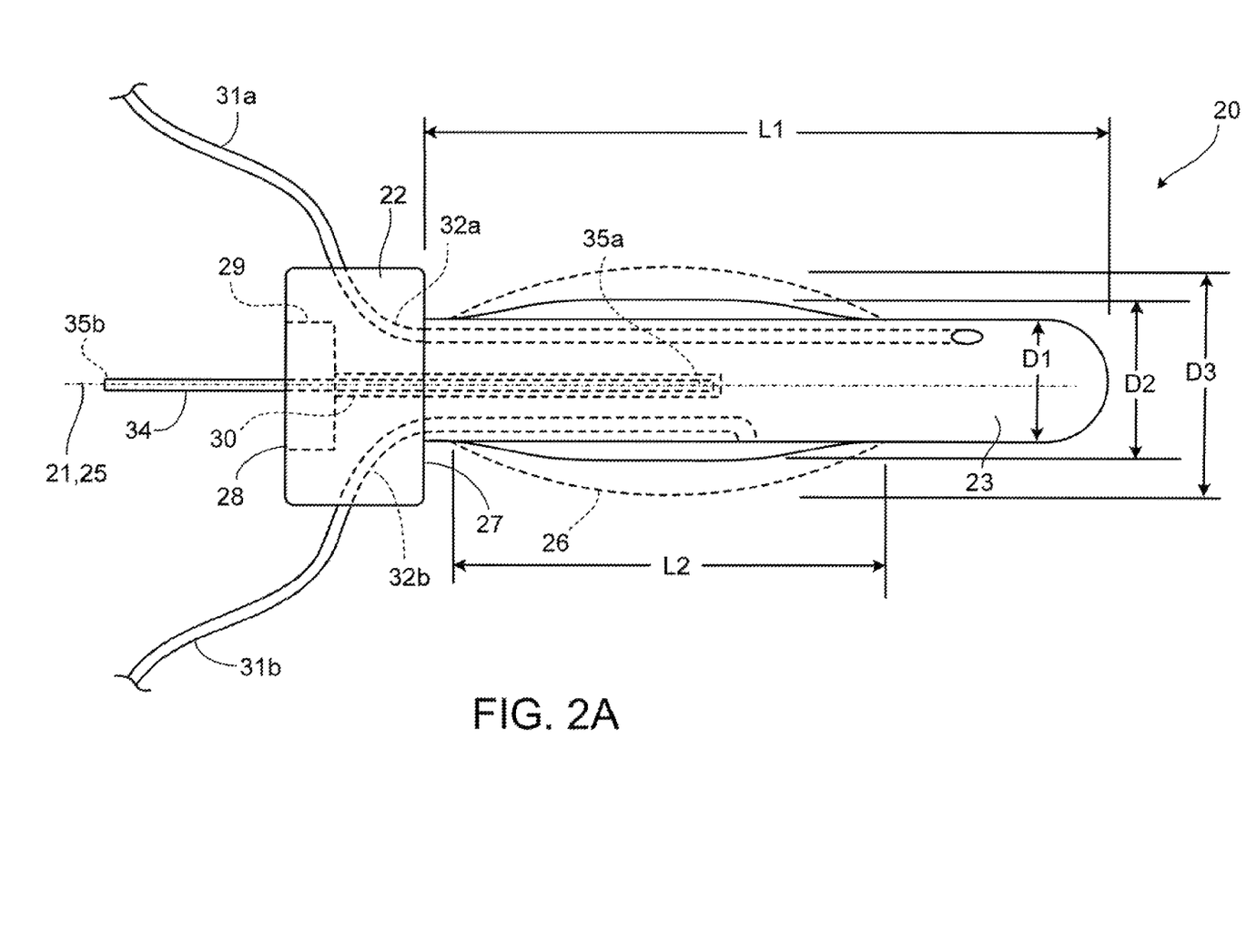
FIG. 2A is a side view of a manipulator tip for a uterine manipulator.
Figure 2B:
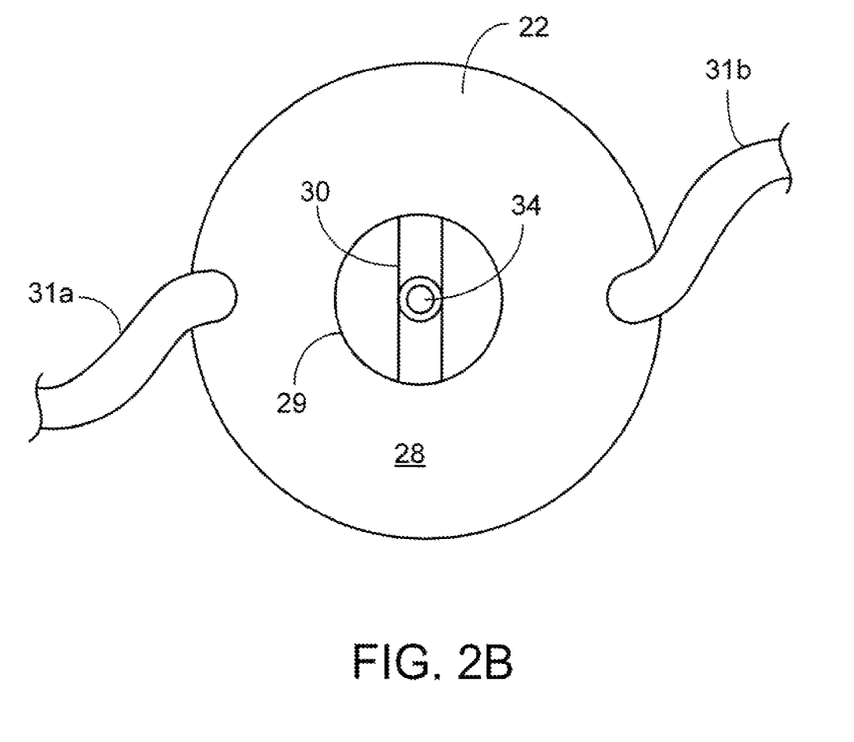
FIG. 2B is a front view of the manipulator tip of FIG. 2A.

Referring to FIGS. 2A and 2B, the manipulator tip 20 includes a tip base 22 and a finger 23 that extends from a first surface 27 of the tip base 22. The finger 23 is configured to be inserted into a cervix. More specifically, the finger 23 is sized to fit within the cervical canal of the cervix without entering the uterine cavity. The finger 23 has a length L1 of about 1 cm to about 5 cm (e.g., 3 cm) along its longitudinal axis 21 and a diameter D1 of about 1 mm to about 6 mm (e.g., about 5.1 mm). The finger 23 carries an expandable balloon 26 that is configured to engage a cervical canal between an internal cervical os and an external cervical os of the cervix. The expandable balloon 26 is shaped to conform to the cervical canal and has sufficient surface area to engage the cervix in a manner that allows for manipulation of the uterus about a pivot point that is within the vaginal canal at or just below the cervix. The expandable balloon 26 can, for example, have an elliptospheric shape (e.g., when expanded or contracted or both) having a longitudinal (major) axis 25 parallel to the longitudinal axis 21 of the finger 23. The expandable balloon 26 has a contracted diameter D2 of about 1.5 mm to about 9 mm (e.g., about 5 mm) or a diameter that is about 0.5 mm to about 3 mm (e.g., about 1 mm) greater than the diameter D1 of the finger 23. The expandable balloon 26 has an expanded diameter D3 of about 3 mm to about 26 mm (e.g., about 14 mm) or a diameter that is about 1 mm to about 20 mm (e.g., about 10 mm) greater than the diameter D1 of the finger 23. The expandable balloon 26 has a length L2 of about 1 cm to about 4 cm (e.g., 3 cm) along its longitudinal axis 25.

At a second surface 28, opposite the first surface 27, the tip base 22 defines a counter-bore hole 29 which leads to a rectangular aperture 30. As discussed below, the counter-bore hole 29 and the rectangular aperture 30 allow the tip base 22 to be mounted to the manipulator handle 40. Catheter tubes 31a, 31b are connected to the tip base 22 and include a dye catheter tube 31a and a balloon catheter tube 31b. The manipulator tip 20 can include a dye conduit 32a that provides for fluid communication between the dye catheter tube 31a and a tip bore 33 which extends through the finger 23. The dye catheter tube 31a and the dye conduit 32a can be used for delivering a liquid based dye to the tip base 22 for chromopertubation procedures. The manipulator tip 20 also includes a balloon conduit 32b that provides for fluid communication between the balloon catheter tube 31b and the expandable balloon 26. The balloon catheter tube 31b and the balloon conduit 32b allows the expandable balloon 26 to be inflated.

The manipulator tip 20 also includes a rod 34 which includes a distal portion 35a that is disposed within the finger 23, and a proximal portion 35b that extends outwardly from the second surface 28 of the tip base 22. The rod 34 helps to provide the finger 23 with increased resistance to bending. The rod 34 can be formed of any of various relatively rigid materials, including metals and polymers. The manipulator tip 20 including the tip base 22, the finger 23, the expandable balloon 26, and the catheter tubes 31a, 31b can be formed by molding (e.g., extruding, blow molding or injection molding) and can be formed of one or more medical grade materials. Medical grade plastics and/or rubber, e.g., natural or synthetic rubber (e.g., silicone compounds) can be used because of their ease of manufacturing, ready availability and disposable nature.

Figure 3A:
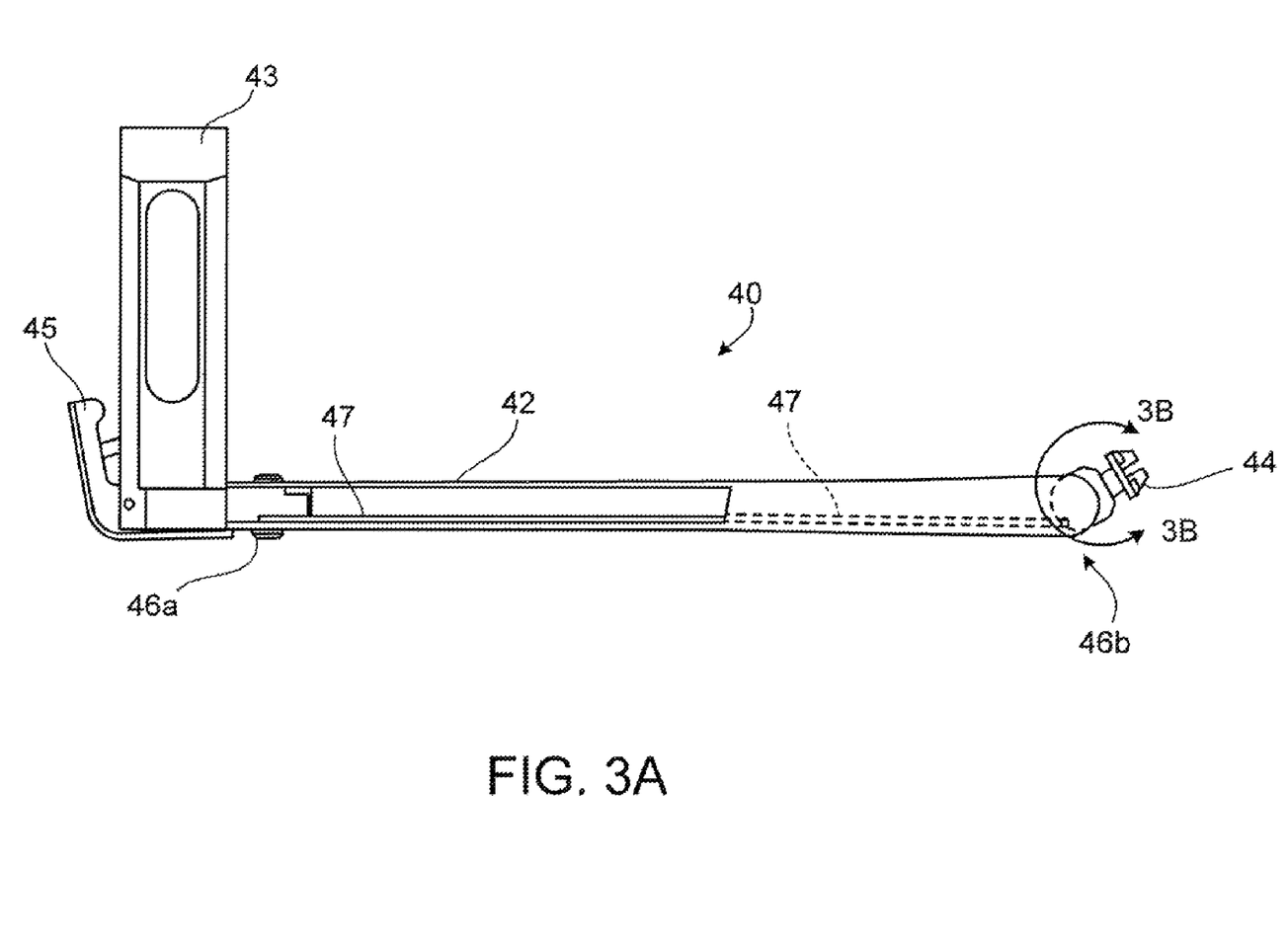
FIG. 3A is a side view of a manipulator handle.

As shown in FIG. 3A, the manipulator handle 40 includes an elongated frame 42, a grip 43, a tip hub 44, and a locking mechanism 45. The frame 42 has a proximal end 46a and a distal end 46b. The grip 43 is affixed in pivotal relationship to the proximal end 46a of the frame 42 and the tip hub 44 is affixed in pivotal relationship to the distal end 46b of the frame 42. A connecting structure 47 operatively couples the tip hub 44 to the grip 43 such that movement of the grip 43 relative to the frame 42 causes a corresponding movement of the tip hub 44 relative to the frame 42. The connecting structure 47 can, for example, be a wire. The locking mechanism 45 is operable to fix the grip 43 against movement relative to the frame 42.

Figure 3B:
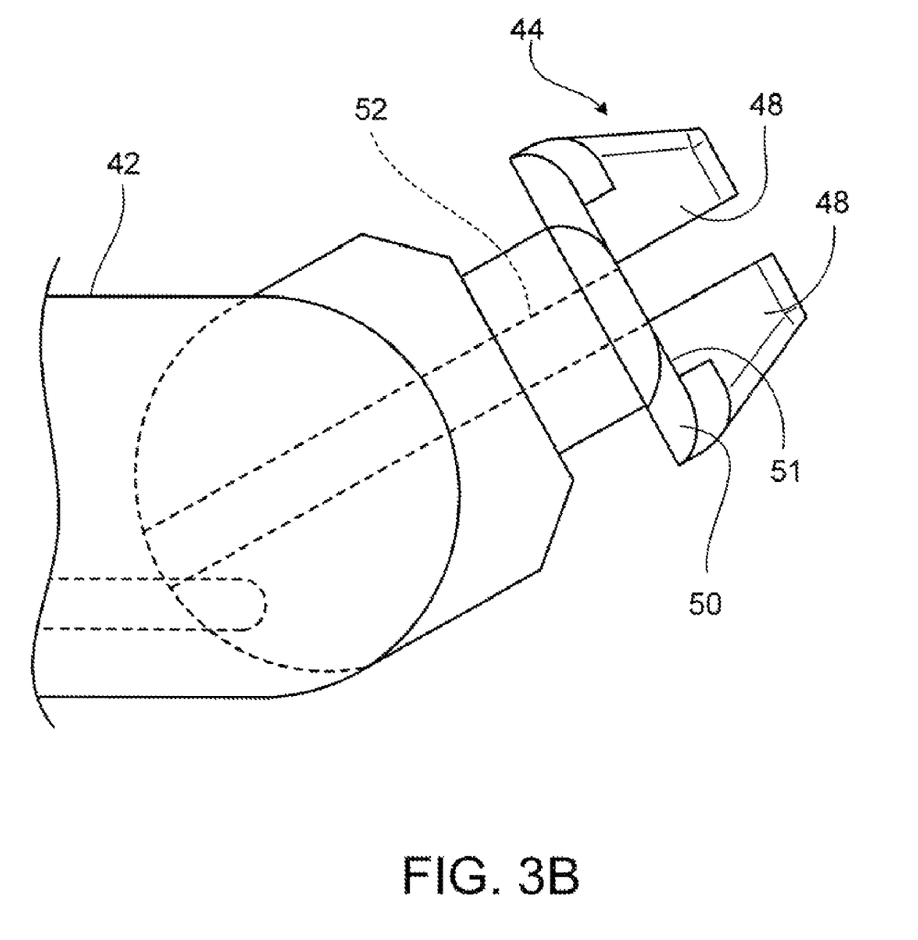
FIG. 3B is a detailed view of a tip hub of the manipulator handle of FIG. 3A.

Referring to FIG. 3B, the tip hub 44 is configured to releasably receive and support the manipulator tip 20 (FIGS. 2A and 2B). In this regard, the tip hub 44 includes a pair of spaced apart flats 48 which extend upwardly from a first surface 51 of a hub base 50. The tip hub 44 can be inserted into the counterbore hole 29 in the tip base 22 and into a position in which the spaced apart flats 48 engage the rectangular aperture 30. The tip hub 44 also includes a hole 52 for receiving the proximal portion 35b of the rod 34. A suitable manipulator handle is commercially available from CooperSurgical, Trumbull, Conn., under the name RUMI® handle.

Figure 4:
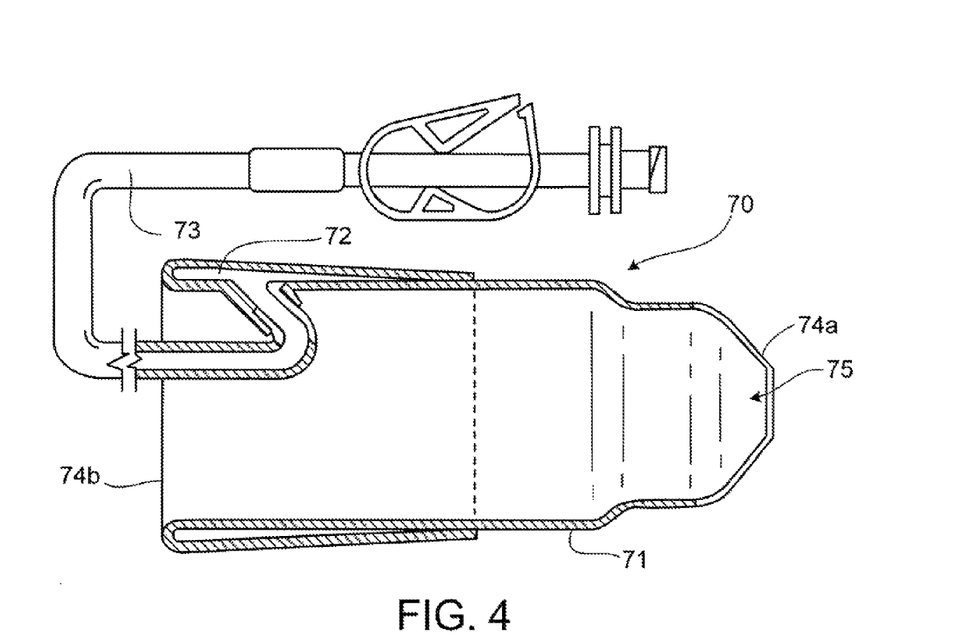
FIG. 4 is a side, partial cross-sectional view of a vaginal occluder.
Figure 5:
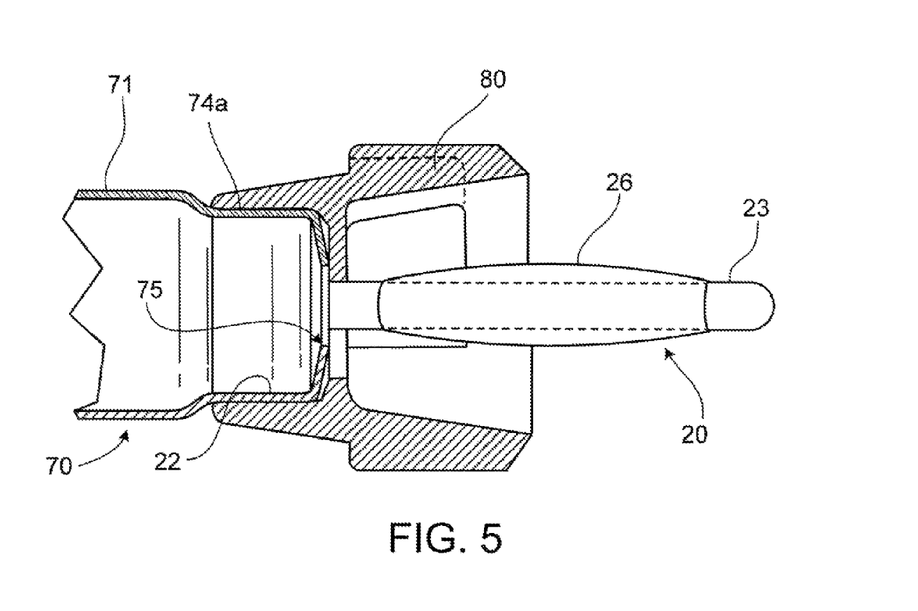
FIG. 5 is a detailed, cross-sectional view of a distal end portion of a uterine manipulator.

Referring to FIG. 4, the vaginal occluder 70 includes a main body 71 including an expandable balloon cuff 72, a balloon cuff catheter tube 73, and main body distal and proximal ends 74a, 74b. The balloon cuff catheter tube 73 is affixed to the balloon cuff 72 and communicates fluid to the balloon cuff 72 when inflation is desired. The vaginal occluder 70 can be constructed of a medical grade silicone suitable for injection molding. The distal end 74a includes an opening 75 having a diameter larger than the finger 23 (FIG. 2A) and smaller than that of the tip base 22. As illustrated in FIG. 5, the opening 75 is sized relative to the diameter of the finger 23 and the tip base 22 to permit the vaginal occluder 70 to be slidably received on the manipulator handle 40 by pulling the proximal end 74b over the manipulator tip 20, such that the balloon cuff 72 is disposed in circumscribing relationship to the frame 42. Further, the vaginal occluder 70 is positioned on the manipulator tip 20 so that the distal end 74a abuts against the first surface 27 of the tip base 22. The cervical cup 80 is then mounted on the tip base 22 with the distal end 74a of the vaginal occluder 70 sandwiched therebetween. Once the vaginal occluder 70 is installed in the above described fashion and the distal end 74a is sandwiched between the tip base 22 and the cervical cup 80, a seal is formed therein to prevent the flow of fluid (i.e., liquids or gases) between the cervical cup 80 and the tip base 22 during surgical procedures. The sandwich-like engagement of the distal end 74a between the tip base 22 and the cervical cup 80 also anchors the distal end 74a to the tip base 22 when the proximal end 74b of the vaginal occluder 70 is caused to be stretched in a direction opposite the distal end 74a. Suitable vaginal occluders are commercially available from CooperSurgical, Trumbull, Conn., under the name Colpo-Pneumo Occluder™.

Figure 6A:
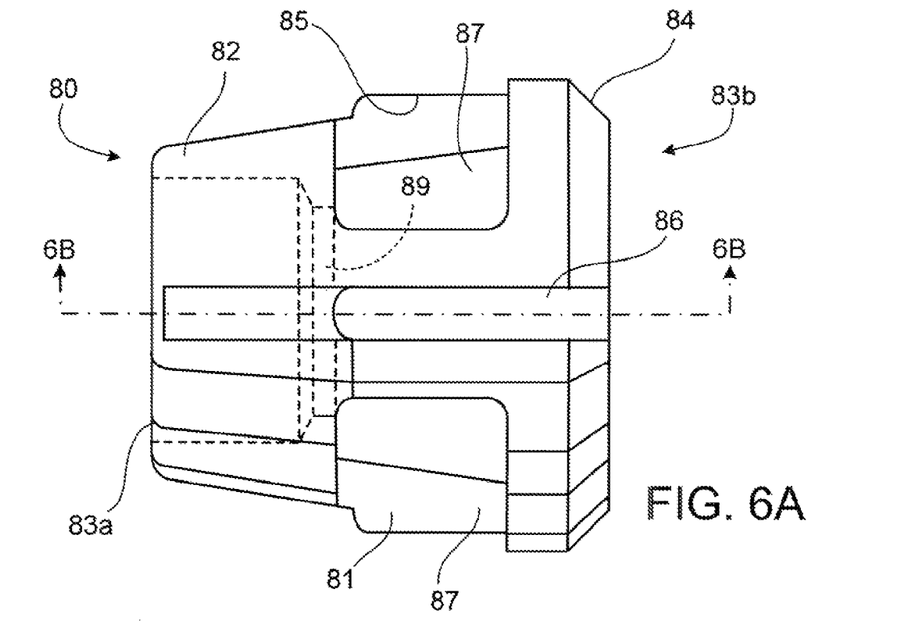
FIG. 6A is a side view of a cervical cup.
Figure 6B:
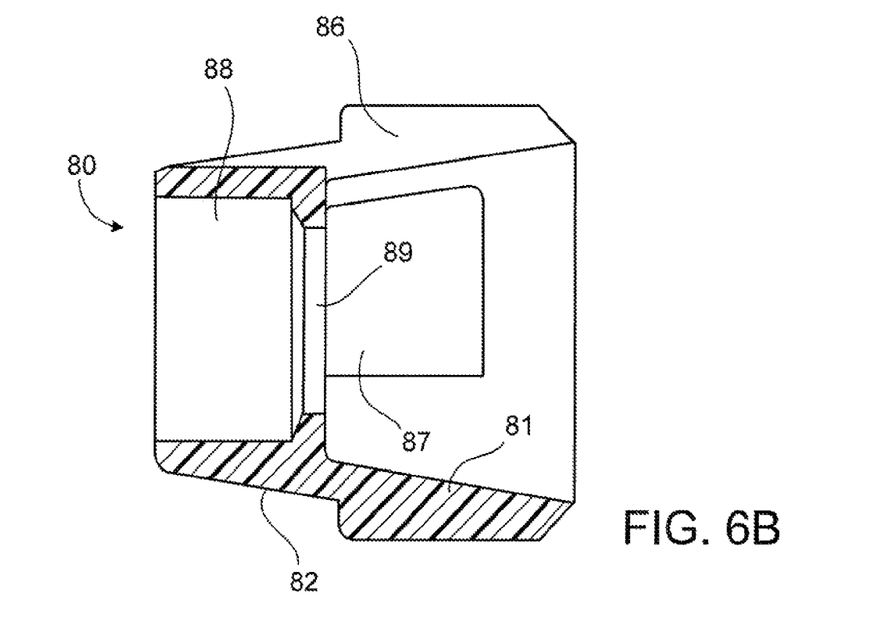
FIG. 6B is a cross-sectional view of the cervical cup of FIG. 6A, taken along line 6B-6B.

Referring to FIGS. 6A and 6B, the cervical cup 80 includes the annular body 81, a cup base 82 at a proximal end 83a and a rim 84 at a distal end 83b. The rim 84 is beveled to permit an anatomical landmark and incision backstop during use. The cervical cup 80 is formed of a material suitable for medical devices, that is, a medical grade material. Plastics, such as polyvinylchloride, polycarbonate, polyolefins, polypropylene, polyethylene or other suitable medical grade plastic, or metals, such as stainless steel or aluminum, can be used. The annular body 81 presents an outer peripheral, generally cylindrical surface 85 which extends between the rim 84 and the cup base 82. A laterally-extending slot 86 is positioned on the cylindrical surface 85 to permit use of surgical instruments. Viewing windows 87 may be disposed in and extend through the outer cylindrical surface 85.

The cup base 82 defines a socket 88 for captively receiving the tip base 22. The cup base 82 also includes an aperture 89 extending between the socket 88 and the annular body 81 for receiving the finger 23 (FIG. 2A) when cervical cup 80 is mounted on the manipulator tip 20. When cervical cup 80 is mounted on the manipulator tip 20, the finger 23 extends axially through annular body 81, as shown in FIG. 1. Suitable cervical cups are commercially available from CooperSurgical, Trumbull, Conn., under the names KOH Cups™ and KOH Cup™.

The uterine manipulator 10 may be used in a number of procedures that require manipulation of the uterus, including surgical procedures, such as hysterectomies. In one example, the uterine manipulator 10 is used in a total laparoscopic hysterectomy (TLH) surgery. A patient is prepared for TLH surgery according to known procedures. Once prepared, the patient's abdominal cavity 102 is inflated with a gas (e.g., $CO_2$) to facilitate accessibility to and visibility of the female pelvic organs, and surgical instruments, including a laparoscope 152, are inserted through the abdomen wall 104 into the abdominal cavity 102, as shown in FIGS. 7 and 8.

Next, the uterine manipulator 10 is inserted into the vaginal cavity 106. When inserted, the cervix 108 is received into the annular body 81 of the cervical cup 80 and the rim 84 is placed into engaging relationship with the apex 109 of the fornix 110. In this position, the cervical cup 80 provides an anatomical landmark at the base of the uterus 112 (i.e., where a cut is to be made) and also helps to inhibit unintended damage to the ureters 114 by pushing them out of the way. The finger 23 is inserted into the cervix 108 such that the expandable balloon 26 is positioned between an internal cervical os 115 and an external cervical os 116. The expandable balloon 26 is inflated to come into engaging relationship with and thereby anchor to the cervical canal 117. The expandable balloon 26 conforms to the cervical canal 117. A large percentage of the surface area of the balloon (e.g., about 90% to about 100%) contacts the wall of the cervical canal 117. The expandable balloon 26 contacts the cervical canal 117 and thereby prevents the manipulator from inadvertently moving relative to the uterus during surgery.

Figure 7:
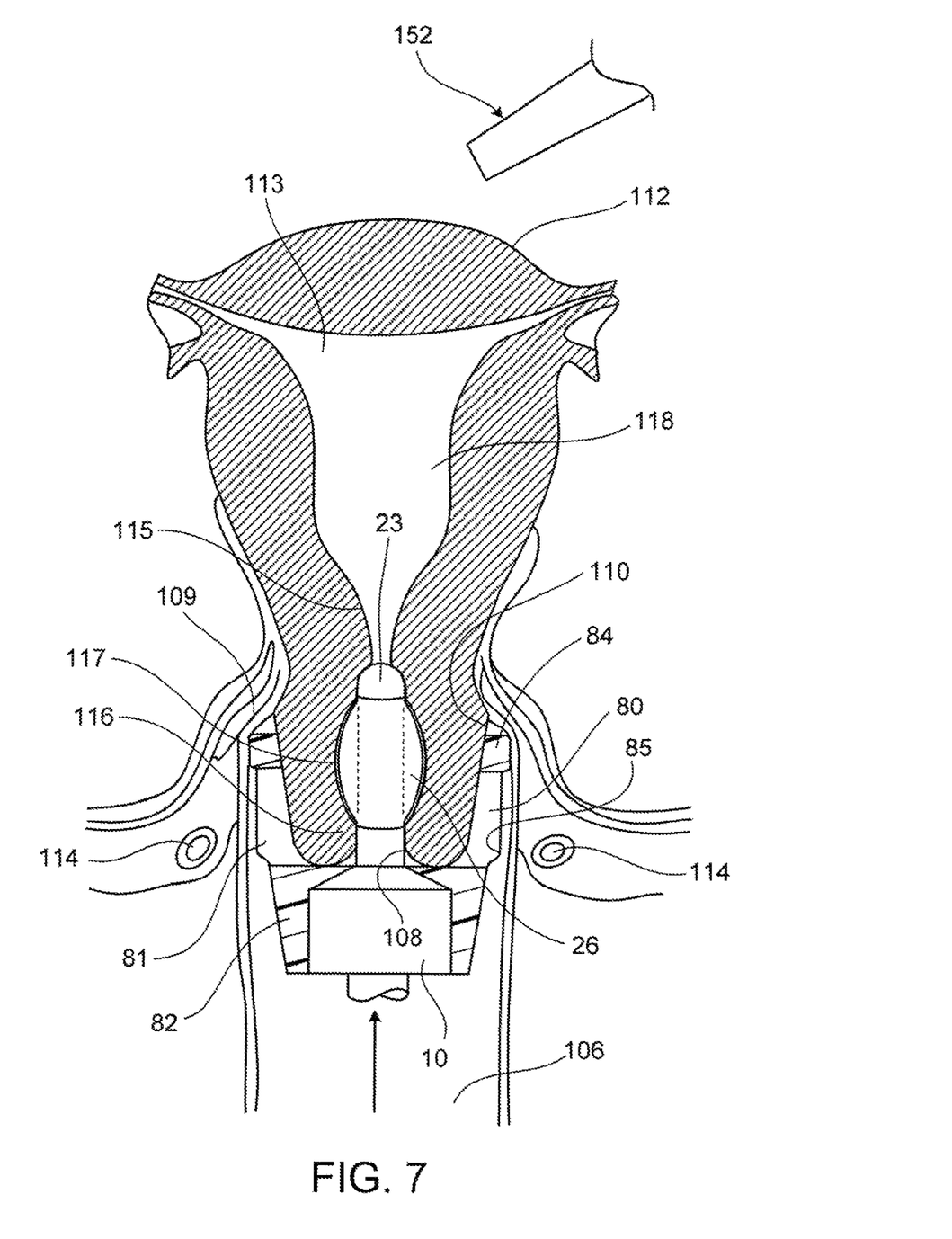
FIG. 7 is an anterior, cross-sectional view of a uterus showing a fully inserted uterine manipulator.
Figure 8:
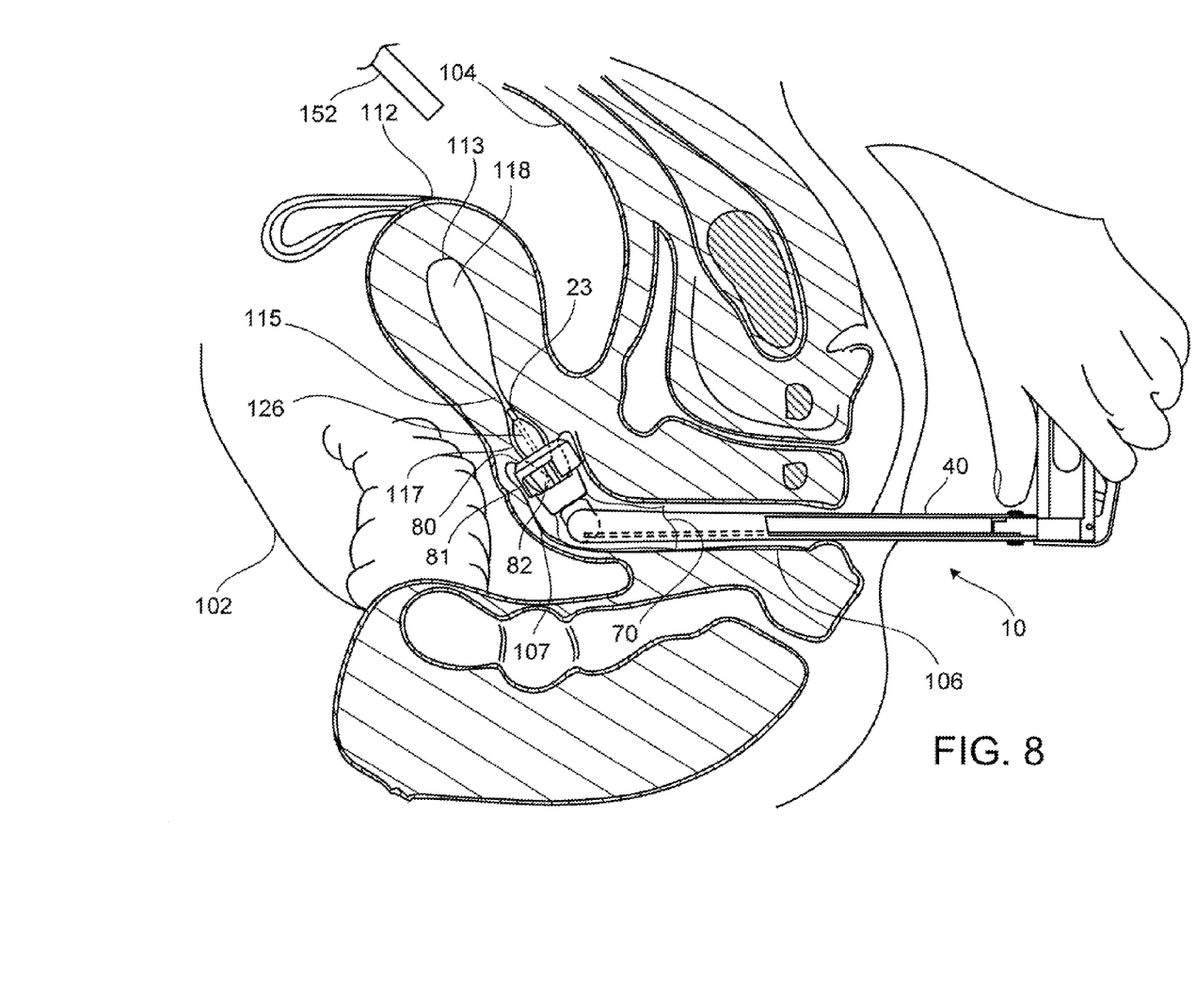
FIG. 8 is a cross-sectional side view of a pelvic cavity showing a uterine manipulator holding a uterus in an anteverted position

As illustrated in FIG. 7, when the uterine manipulator 10 is fully inserted, the finger 23 extends within the cervical canal 117 without entering the uterine cavity 118. Once the uterine manipulator 10 is inserted, the vaginal occluder 70 may be inflated (e.g., with sterile, water-based liquid or gas) to seal the distal vaginal cavity 107 from the proximal vaginal cavity 105. The vaginal occluder 70 inhibits (e.g., prevents) the escape of gas used to inflate the abdominal cavity 102 during and following the first of any colpotomy incisions.

A surgeon or physician can then manipulate or move the uterus 112 into a desired position to perform surgery to cut around the base of the uterus. The finger 23 engages the cervix 108 to permit manipulation of the uterus. The inflated balloon 26 provides sufficient stability to allow this to happen. Because the finger 23 does not enter the uterine cavity 118, likelihood of displacing cancerous cells present in the tissue surrounding the uterine cavity (e.g., in the fundus) is reduced. After the uterus 112 is completely incised such that the uterus 112 is totally free in the abdominal cavity 102 and held only by the uterine manipulator 10, the vaginal occluder 70 is deflated and the uterine manipulator 10 is removed through the vagina.

While certain embodiments have been described above, other embodiments are possible.

As an example, the various components of the uterine manipulator can be permanently attached to one another instead of releasably coupled.

While the use of the uterine manipulator for performing hysterectomy surgery has been described, the manipulator can be used for other types of surgeries or treatments.

While a manipulator handle with a pivotable tip hub has been described, other types of handles can be used. For example, another suitable manipulator handle is commercially available from CooperSurgical, Trumbull, Conn., under the name RUMI Arch™.

Although a manipulator tip that includes a dye conduit, a dye catheter tube and a tip bore for delivering a liquid based dye has been described, in some embodiments, the manipulator tip is not configured to deliver a dye and, thus, does not include a dye conduit, a dye catheter tube, or a tip bore.

Figure 9:
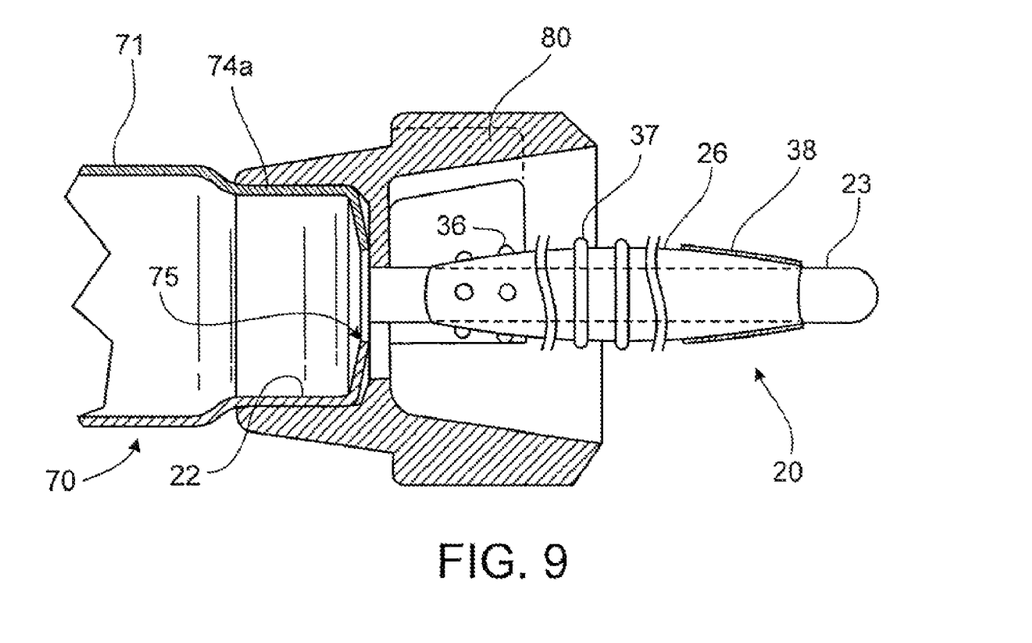
FIG. 9 is a detailed, cross-sectional view of a distal end portion of a uterine manipulator illustrating different surface textures for a manipulator tip.

In some embodiments, the outer surface of the expandable balloon includes a textured surface for enhanced grip. For example, the expandable balloon 26 can include a series of bumps 36 and/or ribs 37, as illustrated in FIG. 9. Alternatively or additionally, the expandable balloon can be provided with a surface treatment, such as a tacky coating 38, for enhanced grip.

Other embodiments are within the scope of the following claims.

What is claimed is:

1. A uterine manipulator tip comprising:
   a finger; and
   an expandable member carried by the finger, wherein the finger has a length of about 10 mm to about 50 mm along a longitudinal axis of the finger, such that the finger is configured to extend within a cervix of a uterus of a patient without entering a uterine cavity of the uterus, and the expandable member is configured to engage a cervical canal between an internal cervical os and an external cervical os of the cervix when the uterine manipulator tip is inserted into the patient and positioned to manipulate the uterus, and wherein the expandable member comprises a textured surface for enhanced grip.

2. The uterine manipulator tip of claim 1, further comprising a base configured to be releasably attached to a uterine manipulator handle, wherein the finger extends outwardly from a first surface of the base.

3. The uterine manipulator tip of claim 1, wherein the finger has a diameter of about 1 mm to about 6 mm.

4. The uterine manipulator tip of claim 1, wherein the expandable member has an expanded diameter of about 2 mm to about 20 mm greater than a diameter of the finger.

5. The uterine manipulator tip of claim 1, wherein the expandable member has a length of about 10 mm to about 40 mm along a longitudinal axis of the expandable member.

6. The uterine manipulator tip of claim 1, wherein the expandable member is a balloon.

7. The uterine manipulator tip of claim 1, wherein the expandable member has an elliptospheric shape when expanded.

8. The uterine manipulator tip of claim 1, further comprising a rod having a distal end extending within the finger providing the finger with increased resistance to bending.

9. The uterine manipulator tip of claim 1, wherein the expandable member comprises a surface treatment for enhanced grip.

10. A uterine manipulator tip assembly comprising:
    a uterine manipulator tip comprising a tip base configured to be releasably attached to a uterine manipulator handle, a finger that extends outwardly from a first surface of the tip base, and an expandable member carried by the finger; and
    a cervical cup that is mountable on the uterine manipulator tip such that a seal is formed between the tip base and the cervical cup, the cervical cup defining a cavity to receive a cervix of a uterus of a patient,
    wherein the finger is configured to extend within the cervix of the uterus without entering a uterine cavity of the uterus and the expandable member is configured to engage a cervical canal between an internal cervical os and an external cervical os of the cervix when the cervical cup is mounted on the uterine manipulator tip and the cervix is received in the cavity of the cervical cup.

11. The uterine manipulator tip assembly of claim 10, wherein the cervical cup comprises an annular member, a cup base, and a rim, wherein the annular member extends between the cup base and the rim.

12. The uterine manipulator tip assembly of claim 11, wherein the annular member defines a portion of a wall of the cavity.

13. The uterine manipulator tip assembly of claim 11, wherein a slot is defined by the annular member, the slot sized to allow passage of surgical instruments through the slot.

14. The uterine manipulator tip assembly of claim 11, wherein one or more windows are defined by the annular member, the one or more windows extending through a wall of the annular member, and the one or more windows configured to allow viewing of the cervix when the cervix is received in the cavity of the cervical cup.

15. The uterine manipulator tip assembly of claim 11, wherein the rim comprises a beveled surface, the beveled surface providing an anatomical landmark and an incision backstop when the cervix is received in the cavity of the cervical cup.

16. The uterine manipulator tip assembly of claim 11, wherein the cup base defines an aperture extending between the cup base and the annular member, wherein the finger extends axially through the annular member.

17. The uterine manipulator tip assembly of claim 10, wherein the finger has a length of about 10 mm to about 50 mm along a longitudinal axis of the finger.

18. The uterine manipulator tip assembly of claim 10, wherein the finger has a diameter of about 1 mm to about 6 mm.

19. The uterine manipulator tip assembly of claim 10, wherein the expandable member has an expanded diameter of about 2 mm to about 20 mm greater than a diameter of the finger.

20. The uterine manipulator tip assembly of claim 10, wherein the expandable member has a length of about 10 mm to about 40 mm along a longitudinal axis of the expandable member.

21. The uterine manipulator tip assembly of claim 10, wherein the expandable member is a balloon.

22. The uterine manipulator tip assembly of claim 10, wherein the expandable member has an elliptospheric shape when expanded.

23. The uterine manipulator tip assembly of claim 10, further comprising a rod having a distal end extending within the finger providing the finger with increased resistance to bending.

24. The uterine manipulator tip assembly of claim 10, wherein the expandable member comprises a textured surface for enhanced grip.

25. The uterine manipulator tip assembly of claim 10, wherein the expandable member comprises a surface treatment for enhanced grip.

* * * * *